United States Patent [19]

Nagaoka et al.

[11] Patent Number: 5,043,278

[45] Date of Patent: Aug. 27, 1991

[54] PHYSIOLOGICALLY-ACTIVE SUBSTANCE FIXED TO A THIN FIBER CARRIER WITH AN ALKYLENE OXIDE CHAIN

[75] Inventors: Shoji Nagaoka; Hajimu Kurumatani; Yuichi Mori, all of Kamakura, Japan

[73] Assignee: Toray Industries, Inc., Japan

[21] Appl. No.: 549,251

[22] Filed: Jul. 6, 1990

Related U.S. Application Data

[63] Continuation of Ser. No. 123,065, filed as PCT JP87/00185 on Mar. 26, 1987, published as WO87/06007 on Oct. 8, 1987, abandoned.

[30] Foreign Application Priority Data

Mar. 28, 1986 [JP] Japan ............................ 61-68494

[51] Int. Cl.$^5$ .................... C12N 11/06; C12N 11/12; G01N 33/549; G01N 33/544
[52] U.S. Cl. ................................. 435/181; 435/177; 435/179; 436/528; 436/530; 436/532; 530/812; 530/813; 530/816
[58] Field of Search ............... 435/174, 177, 188, 181; 530/812, 813, 816; 436/520, 530, 532

[56] References Cited

U.S. PATENT DOCUMENTS

| | | | |
|---|---|---|---|
| 3,844,892 | 10/1974 | Matthews | 435/181 |
| 4,060,597 | 11/1977 | Sato et al. | 436/534 |
| 4,177,038 | 12/1979 | Biebricher et al. | 435/181 X |
| 4,179,337 | 12/1979 | Davis et al. | 435/181 |
| 4,352,884 | 10/1982 | Nakashima et al. | 435/181 X |
| 4,563,425 | 1/1986 | Yoshioka et al. | 435/177 X |

FOREIGN PATENT DOCUMENTS 0134660 3/1985 European Pat. Off. .

OTHER PUBLICATIONS

Ichijo et al., Journal of Applied Polymer Science, vol. 27, 1982, pp. 1665–1674.

*Primary Examiner*—David M. Naff
*Attorney, Agent, or Firm*—Austin R. Miller

[57] ABSTRACT

Fixation of a physiologically active substance on a carrier through an alkylene oxide chain allows the physioactive function of the substance to be retained to a high degree. The fixed physiologically-active substances are useful for separation and purification of materials. The carrier is preferably a thin fiber of 1.0 denier or less, and may be formed from a polymer. The alkylene oxide chain has an amino or epoxy group at one end which bonds to the carrier and a functional group at the other end which bonds to a physiologically-active substance.

7 Claims, No Drawings

PHYSIOLOGICALLY-ACTIVE SUBSTANCE FIXED TO A THIN FIBER CARRIER WITH AN ALKYLENE OXIDE CHAIN

This application is a continuation of application Ser. No. 123,065, filed as PCT JP87/00185 on Mar. 26, 1987, published as WO87/06007 on Oct. 8, 1987, now abandoned.

FIELD OF THE INVENTION

This invention relates to fixed physiologically-active substances and to fixing materials for fixing said physiologically active substances.

BACKGROUND OF THE INVENTION

A number of studies have conventionally been known on the fixation of physiologically active substances on carriers in the solid phase. The main stream of these studies today exists in the fixation of enzymes, although there are many experiments of such kind, including: fixation of immunoreactive substances such as antigens and antibodies for the purpose of obtaining materials for medical treatment; adsorption of particular physioactive substances by means of separation materials in the affinity chromatography; and fixation of tangible components such as useful fungous bodies and cells for use in bioreactors and/or artificial organs.

The word "fixation" herein used indicates that these physioactive substances, originally water-soluble, are made water-insoluble without at all affecting their physiological functions. There are various approaches to the fixation, including carrier bonding, bridging, and integration methods. Of these, the carrier bonding method, which achieves the fixation of a substance through a covalent bond with a carrier, provides the stablest result with the highest bonding power and accordingly with the least disengagement. One of many reported examples of this method is diazo-bonding of a protein (e.g. albumin) for the fixation thereof on a diazonium compound produced by adding dilute sulfuric acid and sodium nitrate to a water-insoluble carrier ($R-NH_2$) containing an amino group. (Chambell et al., Proc Nat Acad Sci , 37, 575 (1951))

Meanwhile, as an improvement of this carrier bonding method, a straight chain structure called a "spacer" or "arm" containing an n-alkyl chain has recently been introduced between the carrier and the physiologically active substance to be bonded. This is because the introduction of such structure allows the physiologically active substance to be fixed at an end of the structure, which reduces steric infection generated form the reaction of the substance with the substrate, thus facilitating it to manifest its function.

Kim et al., for example, fixed heparin, an anti coagulant, on agarose beads containing an n-alkyl chain (wherein n is 2, 4, 8, 10, or 12) as the spacer, and found that the anticoagulating activity measured by the activated part thromboplastin time (APTT) becomes larger with a longer alkyl chain. This phenomenon was named the "spacer effect".

(Kim et al., Thrombosis Research, 26, 43 (1982))

However, a hydrophobic spacer such as an n-alkyl chain has a lower affinity for the physiologically active substances which are essentially water-soluble, and accordingly, the fixation rate may be reduced, or denaturation or deactivation of the physiologically active substances may be caused by the fixation. In addition, since a long n-alkyl chain is water-insoluble without respect to the end functional group, it is necessary to use an organic solvent in order to introduce it into the carrier, and the organic solvent to be used should be selected from an extremely limited range because some carriers are dissolved, denaturated, or damaged by some organic solvents.

Furthermore, on the surface of the carrier which is hydrophobicized by the introduction of such hydrophobic spacer, non-specific adsorption and/or denaturation of other physiologically-active substances, in particular of proteins, tend(s) to occur. This may affect the essential function of the physiologically active substances fixed.

A purpose of this invention is to provide fixing materials for use with physiologically active substances capable of highly revealing physioactive functions thereof when fixed. Another purpose of this invention is to provide fixed physiologically active substances which are fixed by said fixing materials and which have high activity.

DISCLOSURE OF THE INVENTION

The above-mentioned purposes can be attained by introducing an alkylene-oxide chain as a spacer. That is, this invention relates to fixed physiologically-active substances obtained by bonding the physiologically active substances and carriers through an alkylene-oxide chain, and also relates to the fixing materials for use in such bonding.

DESCRIPTION OF THE PREFERRED EMBODIMENT

The alkylene-oxide chain preferably used as the spacer in this invention is either polyethylene oxide or ethylene oxide copolymer having a general formula:

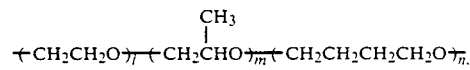

wherein l is an integer in the range from 2 to 100 inclusive; and m and n are 0 or a positive integer; and $$\frac{44\,l}{44\,l\,+\,58\,m\,+\,72\,n} \geqq 0.5$$

When a copolymer is used, it may be either a random or block copolymer, or mixture thereof, but the most preferable spacer is a block copolymer or homo polymer with a degree of polymerization in the range from 2 to 100 and a content of ethylene oxide unit ($-CH_2CH_2O-$) of more than 50 weight %.

The carriers used in this invention at least have a water-insoluble surface. That is, the entire carrier may be composed of a water-insoluble material, or a carrier of water-soluble materials may be covered with a water-insoluble material. Water-insolubility herein used indicates a substantial insolubility in water at 20° C. As such water-insoluble materials, natural or synthetic organic or inorganic polymers are used, including: celluloses such as cellulose acetate; polysaccharides such as dextrin; collagens; polyolefins such as polyethylene and polypropylene; homopolymers or copolymers of vinyl compounds such as vinyl acetate, vinyl chloride, acrylonitrile, acrylic ester, methacrylic ester, and styrene; polyesters such as polyethylene telephthalate and polybutylene terephthalate; and aliphatic and aromatic polyamides. Bridging treatment is performed on these materials when necessary to make them water-insoluble.

Since a carrier of this invention is bonded with an alkylene-oxide chain as a spacer, the carrier must contain a functional group as the connector with the spacer. Accordingly, unless such functional group is contained, activation treatment is performed to introduce a functional group into the carrier. Besides, an alkylene-oxide chain may be introduced by using a monomer which contains an alkyleneoxide chain as the side chain, as the copolymerization component of the polymer of which the carrier is formed, as described later.

The carriers should assume an appropriate form such as a sphere, cylinder, disk, test tube, fiber, film, particle or microtray, according to the application. A particularly preferable form is an extremely thin fiber of less than 1.0 denier. Such fiber may be composed of a polymer including polyester, polyamide, polytetrafluoroethylene, polystyrene, polyolefin, cellulose, polyamino acid, and collagen, although polyester is particularly preferable. When a multi-component fiber is used the polymer which remains should be any of the above mentioned, but polystyrene, polyethylene, water-soluble polyamide, alkaline-solution-soluble polyester, and water-soluble polyvinyl alcohols may be used for other combination components. The extremely thin fibers composed of these polymers are used as the carriers of this invention in the form of a textile, knit, or non-textile organization.

The alkylene-oxide chain can be bonded with the carrier surface, for example, by:

(1) a method which uses a coupling reaction, or (2) a method which uses a polymer or a copolymer comprising a monomer having an alkylene-oxide chain as the side chain and also having a polymerizable carbon-carbon double bond.

Of these, method (1) is preferable, and it is particularly preferable to use an alkylene oxide chain containing an amino group or an epoxy group at an end as the functional group.

In concrete, the bonding is achieved by allowing an excess amount of the alkylene-oxide chain containing an amino group at each end as the functional group to react with the carrier comprising a polymer containing a functional group capable of bonding with the amino group. Such functional group may be an epoxy group, for example; such polymer may be one containing glycidyl methacrylate as a copolymer component, or may be unhardened epoxy resin, for example.

On the other hand, method (2) can use a carrier comprising a water-insoluble copolymer having a monomer unit represented by the formula:

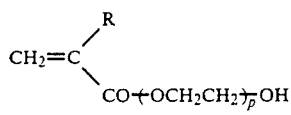

(wherein p is an integer of 2 or more; and R denotes either H or CH$_3$), or a carrier coated with the said monomer.

Anything can be used as the copolymer component only if it can be polymerized with the said monomer and can form a water-insoluble polymer. Methylmethacrylate, acrylonitrile, styrene, and vinylchloride may be given for example. It is also preferable to copolymerize with a bridgeable monomer such as diethylene glycol dimethacrylate.

When the copolymer is used as the coating agent, the thickness of the coating layer is not particularly limited, although 100 A or more is usually preferable. As to the material of the internal part of the carrier, there is no particular limit, but proper selection should be made according to the application from, for example, organic polymers, glass, metals, etc.

The amount of the alkylene-oxide chain bonded with the carrier surface can be controlled arbitrarily by changing the chemical composition of the carrier and/or conditions for the reaction. In order to obtain an effective amount of fixation of the physiologically active substance, it is preferred to bond at least $1 \times 10^{-8}$ mols per cm$^2$ of the carrier.

Fixation of a physiologically active substance on the alkylene-oxide chain bonded with the carrier can be easily attained by introducing a functional group capable of forming a covalent bond with said functional group into the alkylene-oxide chain at an end.

The functional group capable of reacting to form a covalent bond with a physiologically active substance may be an amino, carboxyl, epoxy, hydroxy, carbodiimide, aldehyde, isocyanate, or imidazole group, although hydroxyl, amino, and epoxy groups are particularly preferable because they are easily introduced to an end of the polyethylene-oxide compound. For forming a covalent bond between such functional group and a physiologically active substance, known methods can be used as described, for example, in "Fixed Enzymes" compiled by Ichiro SENBATA, pages 11 to 40, Kodansha (1975).

For example, in case the polyethylene oxide compound bonded with the surface of a water-insoluble carrier contains a free amino group at an end, fixation can be attained by using glutaraldehyde as a binder to form a Schiff base between the amino group in the polyethylene oxide compound and another amino group contained in the physiologically active substance, e.g., a protein.

Or in case the physiologically active substance to be fixed contains a carboxyl group, fixation can be easily achieved on the said carrier only if the substance is treated in advance by a condensing agent such as carbodiimide reagent or Woodward's reagent K (N-ethyl-5-phenyliso oxazolium-3-sulphonate). Examples of the physiologically active substance to be fixed may be given as follows: enzymes such as asparaginase, urease, and urokinase; hormones such as human chrionic gonadotropin, and thyroid stimulating hormone; blood plasma proteins represented by coagulating factors such as albumin, various complement related materials, and thrombin, and anticoagulating factors such as antithrombin III; immunoreactive materials such as mycoplasma antigen and estrogen antigen; muchopolysaccarides such as heparin, heparan sulfuric acid, chondroitin sulfuric acid, and hyaluronic acid; amino acids such as alanine, lysine, glutamic acid, and aspartic acid; various prostaglandin derivatives; glycolipids such as lipopolysaccharide; antibiotics such as polymixin B and chloramphenicol; blood cells such as erythrocyte, leucocyte (granulocyte and macrophage) and lymph; epithelial cells or endothelical cells such as blood vessel endothelical cells, liver cells, and pancreatic B cells; various differentiation and growth factors such as ECFG and CSF relating to the differentiation and/or growth of said cells; and gene-related materials such as DNA and RNA. From these, appropriate substances can be selected according to the application.

The following examples will further illustrate the invention.

EXAMPLE 1 AND COMPARISONS 1 and 2

(Preparation of spacer)

A mixed solution of polyethylene glycol with the degree of polymerization 23 (number average molecular weight 1000) and acrylonitrile was allowed to react for cyanoethylification in the presence of microgranular strong-basic anion exchange resin "Amberlight IRA-400" (Rohm & Haas) so as to produce a polyethylene oxide compound having a β-cyanoethoxy group at each end. Then, 100 g of this compound was dissolved in 1 l of water, followed by introduction of hydrogen to the solution at 60° C. for 6 hours. Thus, 91 g of bisaminopolyethylene oxide compound (PGD-1000) having an amino group at each end and with a degree of polymerization 23 was produced.

(Preparation of carrier)

To prepare the carrier, PGD-1000 prepared as mentioned above was introduced to a film of polyvinyl chloride copolymer containing an epoxy group, in the procedure shown below.

First, polyvinyl chloride (PVC) commercially available was dissolved in 4 l of N,N-dimethyl formaldehyde (DMF). Then, 11 g of sodium diethyldithiocarbamate (PTC) was added to the solution and allowed to react under the light-shielded condition at 50° C. for 3 hours so as to produce photofunctionally DTCed PVC.

Then, 50 g of DTCed PVC thus produced was dissolved in 1 l of tetrahydrofuran (THF). Then, 80 g of glycidylmethacrylate (GMA) was added to the solution and allowed to provide a light graft reaction at 40° C. for 6 hours under the light of a 100-watt high pressure mercury lamp so as to produce a polyvinyl chloride - glycidylmethacrylate graft copolymer (PVC-g-GMA) containing an epoxy group. The graft rate of this copolymer determined by the elementary analysis was 86%.

From a 5% THF solution of this polymer, a film of about 100 μm in thickness was prepared by the solvent cast method using a glass plate. This film was dipped in a 50% solution of PGD-1000 and allowed to react at 60° C. for 24 hours so that the spacer was introduced onto the film surface.

In accordance with the method of determination of the introduced amino group using the adduct formation of benzilamine and 2-hydroxy-1-naphtylamid (HNA) (C. D. Ebert et al., J. Biomed. Mater. Res., 16, 629 (1982)), the amount of PGD-1000 introduced to the film surface was determined to be 0.7 μmol/cm². In addition, from the decrease in the water contact angle at the film surface from 65° to 43° due to the introduction of PGD-1000 (with the measurement made by using a contact angle measuring instrument type CA-P of Kyowa Kagaku K.K.), it was found that the film surface was evidently hydrophilicized.

(Fixation of heparin)

In a glass vessel, 800 mg of sodium heparin and 0.07 g of Woodward's reagent K were dissolved in 100 ml of phosphoric buffer solution of isotonic sodium chloride (PBS), and then gently stirred at 4° C. for 8 hours to activate heparin. In this activated-heparin solution, said PGD-1000-introduced film was dipped to allow a time reaction at 4° C. for fixation of heparin on the film surface.

After completion of the reaction, the film was washed three times with PBS to remove unfixed heparin. Then, 2M ethanol amine PBS solution which was adjusted in advance to pH7.4 with hydrochloric acid was added to permeate at 4° C. for 24 hours so as to block the residual active group of heparin. On the heparin-fixed film surface thus obtained, 0.2 mg/cm² of heparin was found to have been fixed, as a result of ESCA (Electron Spectroscopy for Chemical Analysis) (which was executed by using an X-ray electron spectroscope ESCA750 of Shimazu).

(Measurement of activity of heparin)

The activated part thromboplastin time (APTT) was used to measure the anticoagulating activity of the fixed heparin.

In more detail, using a 3.8% solution of sodium citrate as the anticoagulant, a test was made on the bovine blood plasma from which the cell components were removed in advance by centrifugation. Into 1 ml of this plasma, the heparin-fixed film having the surface area of 20 cm² was introduced, and the mixture was stirred at 37° C. for 30 minutes. Then, the plasma was separated from the film, and poured into a test tube of silicone coated glass, to which 0.1 ml of activated phospholipid agent was further added. This mixture was kept at 37° C. for 30 seconds, and then heated for 5 minutes. After that, 0 1 ml of 1/40 M CaCl₂ solution was added to this test tube, which was then allowed to stand at 37° C. for 30 seconds and was inclined gently. In this situation, the duration of fibrin precipitation was measured at APTT.

For comparison, carriers containing hexamethylenediamine and diaminododecane respectively as a spacer were prepared, heparin was fixed on them, and the activity of heparin was measured all under just the same conditions. The result of measurement was given in Table 1.

TABLE 1

| | Activity of heparin fixed on polyvinyl chloride films containing various spacers | | | | |
| --- | --- | --- | --- | --- | --- |
| | Spacer | Structural Formula | Amount of Spacer Introduced (μmol/cm²) | Amount of Fixed Heparin (μg/cm²) | APTT (sec) |
| Control (PVC-g-GMA film) | nil | | nil | nil | 20 ± 1 |
| Example 1 | PGD-1000 | $+CH_2CH_2O+_{23}$ | 0.7 | 10 | 200 ± 6 |
| Comparison 1 | Hexamethylenediamine | $+CH_2+_6$ | 0.8 | 11 | 43 ± 5 |
| Comparison 2 | Diaminododecane | $+CH_2+_{12}$ | 0.7 | 9 | 70 ± 2 |

As seen from the above table, the coagulating activity of heparin fixed by using the spacer of this invention was far higher than those of heparin fixed by using hydrophobic n-alkyl spacers of the prior art.

EXAMPLE 2 AND COMPARISON 3

Into 1000 g of isopropanol, 120 g of methylmethacrylate (MMA), 80 g of polyethyleneglycolmonomethacrylate ("Blenmer-PE-350" of Nihon Yushi K.K. which has the polyethyleneglycol ethyleneglycol part with the number average degree of polymerization 9), and 1.4 g of $\alpha,\alpha'$-azobis ($\alpha,\alpha'$-dimethylvaleronitryl) were added and allowed to react at 50° C. in the flow of nitrogen gas. After 5 hours, the polymerized solution obtained was transferred to a vessel having 2 mm small holes in the bottom, through which holes the solution was allowed to go down from the height of 1 m into the cool water continuously stirred. Thus, polymer particles of 50 to 100 μm in diameter could be obtained. By ESCA analysis, about 20 mmol/g of polyethyleneglycol chain was found on the surface of these polymer particles.

Then, 10 g of these polymer particles was sufficiently washed with water, and allowed to suspend in 180 ml of 1 M NaOH solution, to which 10 ml of epichlorohydrin was further added. Then, the mixture was violently stirred for reaction at the room temperature for 24 hours. After completion of the reaction, the carrier containing the spacer of epichlorohydrine activated polyethylene oxide was collected, and the excessive epichlorohydrin was washed out. This carrier was allowed to suspend in the 2M potassium carbonate buffer solution containing 3 g of sulfanilic acid (pH10). This mixture was again adjusted to pH10, and then allowed to stand for 6 days. Phloroglicinol was allowed to work on the carrier thus obtained so as to produce a phloroglicinol derivative, to which 5% divinyl sulfone was added to react at pH11 for 30 minutes. Then, under the condition of pH9, a soybean trypsin inhibitor was added as a ligand.

By this method, the carrier could be obtained on which the soybean trypsin inhibitor was fixed and which contained polyethylene oxide as the spacer.

For comparison, polymer particles were produced by using hydroxyethylmethacrylate as the copolymer component of MMA, and the soybean trypsin inhibitor was fixed on the carrier in just the same way as described above.

The result of comparison of the trypsin adsorption capacity is shown in Table 2.

TABLE 2

Trypsin adsorption capacity of various carriers

| | Spacer (Structural Formula) | Amount of Trypsin Inhibitor Fixed (in mg or ml for wet carrier) | Tripsin Adsorption Capacity (in mg or ml for wet carrier) |
|---|---|---|---|
| Example 2 | $-(CH_2CH_2O)_9-$ | 15 | 5 |
| Comparison 3 | $-CH_2CH_2-$ | 2 | 0.8 |

As shown above, the adsorbate obtained in accordance with this invention provided a higher adsorption capacity.

EXAMPLE 3 and COMPARISON 4

Four hundred grams (400 g) of the sea island type of complex fiber having 50 parts of polypropylene (Mitsui "Noblen" J3HG) as the island component and having a mixture of 46 parts of polystyrene ("Styrop" 679) and 4 parts of polypropylene (Sumitomo "Reblen" WF-727-F) as the sea component was dipped in a mixture solution comprising 560 g of N-methylylole-chloroacetamide, 3100 ml of nitrobenzene, 2020 ml of conc, sulfuric acid, and 8 g of paraformaldehyde, and allowed to react at 20° C. for one hour. Then, the fiber was removed from the reaction solution, and put into 5 l of ice water at 0° C. to stop the reaction. Then, it was washed with water, followed by extraction and removal of nitrobenzene from the fiber by using methanol. The fiber was vacuum dried at 40° C. to produce the chloroacetamidemethylified fiber (fiber A).

This fiber was 0.5 deniers in diameter. Now, 3000 ml of 20 wt % dimethylsufoxide solution of the same bisaminopolyethyleneoxide compound (PGD-1000) as used in example 1 was added to 80 g of said fiber A, and allowed to stand for reaction at the room temperature for 48 hours. Then, the fiber was washed with 20 l of water, and then with 1N HCl. It was further washed with 20 l of water to produce the fibre to which the polyethylene oxide chain with an amino group at an end was introduced.

Into a flask, 1.3 g of this fiber was put, and 3% phosphoric buffer solution of isotonic sodium chloride (PBS) was added. The flask was then shaken at the room temperature for 4 to 5 hours.

To the fiber sufficiently washed with PBS, 2.5 wt %. aqueous solution of polypeptide antibiotic polymixin sulfate B (Fiser Co.) and 7 ml of PBS was added, and the fixture was gently stirred for fixation at 4° C. for 24 hours. Then, it was dipped in this buffer solution at 4° C. for 24 hours to block the residual free amino group. Then, the fiber was transferred into 5 ml of 0.1 wt % PBS solution of sodium boron hydride, and stirred at the room temperature for 24 hours to reduce the formed Schiff base. A polymixin-B fixed fiber (PMX-PEO) was thus obtained.

The amount of polymixin B fixed on this fiber was measured by amino acid analysis, and the result was 3.5 mg/g-fiber.

For comparison, a fiber (PMX-$C_{12}$) on which polymixin B was fixed with diaminododecane used as the spacer was obtained, in just the same way as described above. The amount of polymixin B fixed on this fiber was found to be 3.8 mg/g-fiber.

Using *E. coli* (ATCC25922), antibacterial activity of these fibers was measured, and the result was obtained as shown in Table 3.

TABLE 3

Antibacterial activity of fibers on which polymixin B is fixed

| | Initial Concentration | After 1 hr. Shaking | After 4 hr. Shaking |
|---|---|---|---|
| Bacterial solution (control) | $1.1 \times 10^6$ bacteria/ml | $1.0 \times 10^6$ bacteria/ml | $0.7 \times 10^6$ bacteria/ml |

TABLE 3-continued

| | Antibacterial activity of fibers on which polymixin B is fixed | | |
|---|---|---|---|
| | Initial Concentration | After 1 hr. Shaking | After 4 hr. Shaking |
| Example 3 Number of bacteria in contact with PMX-PEO | $1.1 \times 10^6$ bacteria/ml | $3.1 \times 10^3$ bacteria/ml | $1.0 \times 10^2$ bacteria/ml |
| Comparison 4 Number of bacteria in contact with PMX-C$_{12}$ | $1.1 \times 10^6$ bacteria/ml | $7.2 \times 10^5$ | $3.5 \times 10^5$ |

Condition for experiment:
1 g of each polymixin-B fixed fiber was dipped in 30 ml of bacterial solution, and after shaking the solution at 37° C., the number of bacteria was measured.

As shown above, polymixin B fixed by using the spacer of this invention indicated higher antibacterial activity than the case of the alkyl spacer.

INDUSTRIAL APPLICABILITY

The fixing materials of this invention for use with the physiologically active substances can provide fixation while highly keeping the physioactive function of such substances. Accordingly, the physiologically active substances fixed by using said fixing materials can be used for the base materials of affinity chromatography for the purpose of separation and/or purification of materials, kit components for medical diagnostics and treatment, and implant materials for the organs in the living body.

What is claimed is:

1. A fixing material for use with physiologically active substances, said fixing material consisting essentially of an alkylene oxide chain which is bonded at one end to a water-insoluble carrier in the form of a thin fiber of 1.0 denier or less, and said alkylene oxide chain having an amino or oxy group at said one end capable of bonding with said carrier and a functional group at the other end capable of reacting with the physiologically active substances, wherein the alkylene oxide is a polymer having the formula:

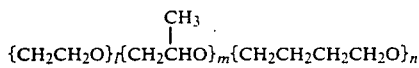

wherein l is an integer of value in the range from 2 to 100 inclusive; and m and n are 0 or a positive integer; and $$\frac{44\,l}{44\,l + 58\,m + 72\,n} \geq 0.5.$$

2. A fixing material for use with physiologically active substances according to claim 1, wherein both m and n are 0 (zero).

3. A fixing material for use with physiologically active substance according to claim 1, wherein the functional group is selected from the group consisting of amino, carboxyl, epoxy, hydroxy, carbodiimide, aldehyde, isocyanate, and imidazole groups.

4. The fixing material defined in claim 1, wherein said thin fiber is a composite sea island fiber having in cross section at least one island surrounded by a sea.

5. A fixed physiologically-active substance consisting essentially of a physiologically active substance bonded to a water-insoluble carrier in the form of a thin fiber of 1.0 denier or less, and is bonded through an alkyleneoxide chain having an amino or oxy group at one end, capable of bonding with said carrier and a functional group at the other end capable of reacting with the physiologically-active substance, wherein the alkylene oxide chain is a polymer having the formula:

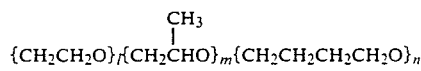

wherein l is an integer of value in he range from 2 to 100 inclusive; and m and n are 0 or a positive integer; and $$\frac{44\,l}{44\,l + 58\,m + 72\,n} \geq 0.5,$$

said physiologically-active substance and said alkyleneoxide chain being bonded by a covalent bond.

6. A fixed physiologically-active substance according to claim 1, wherein both m and n are 0 (zero).

7. The fixed physiologically-active substance defined in claim 5, wherein said thin fiber is a composite sea island fiber having in cross section at least one island surrounded by a sea.

* * * * *

UNITED STATES PATENT AND TRADEMARK OFFICE
CERTIFICATE OF CORRECTION

PATENT NO. : 5,043,278
DATED : August 27, 1991
INVENTOR(S) : Shoji Nagaoka; Hajimu Kurumatani; Yuichi Mori It is certified that error appears in the above-identified patent and that said Letters Patent is hereby corrected as shown below:

In Column 6, line 44, "0 1 ml" should be changed to --0.1 ml--.

Signed and Sealed this

Twenty-third Day of March, 1993

Attest:

STEPHEN G. KUNIN

*Attesting Officer*  Acting Commissioner of Patents and Trademarks